United States Patent [19]

Yasuda

[11] 4,346,174

[45] Aug. 24, 1982

[54] PROCESS FOR ISOLATING SUPEROXIDE DISMUTASE FROM RED BLOOD CELLS

[75] Inventor: Takamasa Yasuda, Tokyo, Japan

[73] Assignee: Fujizoki Pharmaceutical Co., Ltd., Tokyo, Japan

[21] Appl. No.: 275,392

[22] Filed: Jun. 19, 1981

[30] Foreign Application Priority Data

Jun. 23, 1980 [JP] Japan ................................. 55-83920

[51] Int. Cl.$^3$ .............................................. C12N 9/02
[52] U.S. Cl. .................................... 435/189; 435/192; 435/816; 260/113
[58] Field of Search ................ 435/189, 192; 424/177; 260/113

[56] References Cited

U.S. PATENT DOCUMENTS

| | | | |
|---|---|---|---|
| 3,579,495 | 5/1971 | Huber | 260/115 |
| 3,624,251 | 11/1971 | Huber | 260/113 |
| 3,687,927 | 8/1972 | Huber | 260/113 |
| 3,763,137 | 10/1973 | Huber et al. | 260/113 |
| 3,813,289 | 5/1974 | Huber et al. | 260/113 X |
| 3,832,338 | 8/1974 | Huber et al. | 260/113 |

OTHER PUBLICATIONS

McCord et al., Journal of Biological Chemistry, vol. 244, pp. 6049–6055, (1969).

*Primary Examiner*—Lionel M. Shapiro
*Attorney, Agent, or Firm*—Burgess, Ryan and Wayne

[57] ABSTRACT

A process for isolating superoxide dismutase from red blood cells comprising the steps of heating hemolyzed red blood cells in the presence of at least one monovalent inorganic neutral salt and at least one transition metal salt; eliminating precipitate from the hemolyzed red blood cells by filtration or centrifugation to obtain a solution; adding further at least one transition metal salt at least once to the solution under application of heat thereto; and eliminating precipitate from the solution.

19 Claims, No Drawings

PROCESS FOR ISOLATING SUPEROXIDE DISMUTASE FROM RED BLOOD CELLS

BACKGROUND OF THE INVENTION

The present invention relates to a novel process for isolating superoxide dismutase from red blood cells and more particularly to a process for isolating superoxide dismutase from hemolyzed red blood cells by causing proteins having affinity for hemoglobin and superoxide dismutase and other unnecessary proteins to precipitate from the hemolyzed red blood cells in the presence of monovalent inorganic neutral salts and transition metal salts by the application of heat.

Superoxide dismutase is an enzyme which catalyses disproportionation of superoxide $O_2^-$ ions as follows:

$$2O_2^- + 2H^+ \rightarrow O_2 + H_2O_2$$

This enzyme is widely distributed in animal and plant organisms and has the function of eliminating active oxygen from those organisms, which active oxygen is generated in the course of biochemical reactions in the organisms and works as a cytotoxin in the organisms.

Superoxide dismutase obtained in its pure state from the red blood cells of higher animals is a protein metal chelate, which is named "orgotein."

Bovine erythrocyte superoxide dismutase has a molecular weight of 31,200 and consists of two apparently identical sub-units of the molecule, each sub-unit having 151 amino acids, the greater part of the amino acids having a β-type cylindrical structure and the remainder having an α-type spiral structure.

Due to the structures of the amino acids, bovine erythrocyte superoxide dismutase is very resistant to denaturation.

As mentioned above, bovine erythrocyte superoxide dismutase is a protein metal chelate, in which copper and zinc are each contained in an amount of 2 gram atoms per mole of the superoxide dismutase.

The isoelectric point of the superoxide dismutase is near pH 5.5.

Superoxide dismutase is innocuous to living organisms and, immunologically, it cannot be regarded as a foreign material in living organisms and therefore it is an injectable protein.

Pharmacologically, superoxide dismutase can serve as a medicine for treatment of inflammation caused by autoimmune diseases, and, recently, by use of superoxide dismutase, there have been attempts to develop medicines for the treatment of arthritis deformans and chronic rheumatism and for treatment of harmful side effects caused by radio therapy.

Conventionally, several methods of isolating erythrocyte superoxide dismutase, namely "orgotein," from red blood cells, have been proposed. However, those conventional methods have a variety of shortcomings. For instance, the purity and yield of the erythrocyte superoxide dismutase obtained are low and preserved blood cannot be employed for producing the erythrocyte superoxide dismutase by those conventional methods. As a matter of fact, if preserved blood could be employed for producing erythrocyte superoxide dismutase in practice, it would be extremely useful.

More specifically, in Japanese Patent Publication Ser. No. 53-31206, there is disclosed a method of isolating orgotein from hemolyzed red blood cells by subjecting the hemolyzed red blood cells to heat treatment in the presence of salts of divalent metals, such as copper, zinc, cobalt, manganese and magnesium, and causing hemoglobin and carbonic anhydrase to precipitate and removing the same.

In this method, although the hemolyzed red blood cells are treated at a comparatively high temperature for a long period of time, separation by precipitation of unnecessary proteins from the hemolyzed red blood cells for isolation of superoxide dismutase is incomplete and red colored hemoglobin remains in the supernatant solution of the heat-treated hemolyzed red blood cells. The unseparated unnecessary proteins cause degrading of the activity of superoxide dismutase during the next purification process of superoxide dismutase. Furthermore, in this method, when lyophilized red blood cells are employed for isolating superoxide dismutase therefrom, separation and purification of superoxide dismutase are more difficult in comparison with the case where untreated fresh red blood cells are employed.

In Japanese Patent Publication Ser. No. 45-39832, there is disclosed a method of isolating orgotein by treating hemolyzed red blood cells with an organic chlorine compound to form a complex compound of hemoglobin and removing hemoglobin in complex-compound form from the hemolyzed red blood cells. In this method, however, a significant amount of superoxide dismutase is attracted to the complex compound and the yield of superoxide dismutase in the supernatant solution of the hemolyzed red blood cells is decreased by more than 20%.

In the Journal of Biochemical Chemistry, Vol. 224, 6051, there is disclosed another method of isolating superoxide dismutase from hemolyzed red blood cells by use of a chlorine compound. In this method, however, the activity of superoxide dismutase is decreased by at least 20% in the first extraction step, in comparison with the activity of unisolated superoxide dismutase.

These superoxide isolation methods using organic chlorine compounds require a large quantity of organic solvent and therefore are not practical in terms of cost and separation efficiency. Furthermore, when lyophilized blood cells are employed, unnecessary proteins including hemoglobin, to which superoxide dismutase is attracted, remain in the supernatant solution of the hemolyzed red blood cells. Therefore, isolation of superoxide dismutase from tne supernatant solution and purification thereof are extremely difficult.

In Japanese Laid-open Patent Application Ser. No. 49-50195, there is disclosed a further method of isolating superoxide dismutase from hemolyzed red blood cells, which method comprises the steps of subjecting the hemolyzed red blood cells to heat treatment; processing the supernatant solution of the heat-treated hemolyzed red blood cells with a proteolytic enzyme; and filtering the processed supernatant solution and separating and purifying superoxide dismutase from the solution by column chromatography and gel-filtration. The shortcomings of this method are that the steps involved in the process using the proteolytic enzyme are complicated and, when old blood cells or lyophilized blood cells are used for producing superoxide dismutase, superoxide dismutase is tightly bonded to unnecessary proteins contained in the blood cells and therefore purification of superoxide dismutase is extremely difficult.

Finally, in Japanese Patent Publication Ser. No. 53-22137, there is disclosed a method of isolating superoxide dismutase from hemolyzed red blood cells by allowing superoxide dismutase contained in hemolyzed red blood cells to be directly attracted to a weak basic ion-exchange resin. In terms of cost and efficiency, this method, however, is not suitable for separation of such a protein as superoxide dismutase contained in an amount ranging from 0.3 to 0.5 weight percent from other proteins. As a matter of fact, this method cannot be employed for producing a large amount of superoxide dismutase from hemolyzed blood cells.

As described above, those conventional superoxide dismutase isolation methods have a variety of shortcomings and cannot be used in practice.

SUMMARY OF THE INVENTION

It is therefore an object of the present invention to provide a novel process for isolating superoxide dismutase from red blood cells by removing unnecessary proteins, including hemoglobin, and a protein having affinity for superoxide dismutase therefrom, which process is simple and efficient for isolating superoxide dismutase.

Another object of the present invention is to provide a process capable of isolating superoxide dismutase not only from fresh red blood cells, but also from preserved red blood cells, with substantially the same high yield of superoxide dismutase.

The inventor of the present invention has discovered that the most significant obstacle to the separation and purification of superoxide dismutase from hemolyzed red blood cells is a certain protein which can easily form a complex compound in combination with hemoglobin and/or superoxide dimutase, and which protein is difficult to separate from superoxide dismutase. This protein, from its behavior during denaturation thereof, is considered to be lipoprotein derived from blood cell membranes, and hereinafter it is referred to as the affinity protein.

The inventor of the present invention has further discovered that the affinity protein can be easily and completely separated from superoxide dismutase by two or three stepwise heat treatments of the hemolyzed red blood cells in the presence of monovalent inorganic neutral salts and transition metal salts.

The present invention is based on the above-mentioned two discoveries.

DETAILED DESCRIPTION OF THE PREFERRED EMBODIMENTS

When the affinity protein contained in red blood cells and having a strong affinity for superoxide dismutase is processed, for instance, by freezing, lyophilization and treatment by organic solvents, followed by heat treatment, the affinity protein is slightly denaturated in the course of that processing and forms a complex compound in tight combination with hemoglobin and/or superoxide dismutase. Formation of such a complex compound also takes place in the course of aging of red blood cells.

The conventionally encountered difficulty in isolating superoxide dismutase in its pure state from frozen blood cells, lyophilized blood cells and preserved blood is probably due to the presence of a complex of the affinity protein and superoxide dismutase. This is in spite of the fact that frozen blood cells, lyophilized blood cells and preserved blood have been considered to be the most practical superoxide dismutase sources, if superoxide dismutase could be easily separated therefrom in its pure state and with a high yield.

In the present invention, red blood cells that can be employed for isolating superoxide dismutase therefrom are not limited to untreated fresh red blood cells, but aged red blood cells that have preserved for a long period of time, frozen red blood cells and lyophilized red blood cells can be employed as well.

Furthermore, for use in the present invention, while it is preferable to use red blood cells free from blood plasma, red blood cells from which blood plasma has not been completely removed can also be employed without any significant problem.

A process for isolating superoxide dismutase from red blood cells according to the present invention will now be explained. This process substantially comprises two steps.

In the first step, water is added to red blood cells in order to hemolyze red blood cells and facilitate stirring of the hemolyzed red blood cells during the superoxide dismutase isolation process. The amount of water to be added to the red blood cells is 1 to 4 times, preferably 2 to 3 times, the volume of the red blood cells.

The thus formed hemolyzed-red-blood-cell solution is heated at temperatures ranging from 60° C. to 75° C. for 10 to 60 minutes, preferably 65° C. to 70° C. for 25 to 40 minutes, in the presence of a monovalent inorganic neutral salt, such as lithium chloride, sodium chloride, potassium chloride, lithium nitrate, sodium nitrate, potassium nitrate, sodium bromide, potassium bromide, lithium, bromide and ammonium bromide, and a comparatively small amount of a transition metal salt, such as water-soluble salts of copper, cobalt and manganese. Examples of such transition metal salts include Cu(No$_3$)$_2$.3H$_2$O, CuCl$_2$.2H$_2$O, CuBr$_2$, CuCl, MnCl$_2$.4H$_2$O, and CoCl$_2$.2H$_2$O, preferably copper(I) chloride and copper(II) nitrate. The latter copper salts are preferred because they are capable of selectively denaturating the unnecessary proteins and promoting coagulation and precipitation of the same.

The monovalent inorganic neutral salts have the function of separating superoxide dismutase from the affinity protein and unnecessary proteins which mainly include denaturated hemoglobin, by weakening the bonding between superoxide dismutase and the affinity protein and the unnecessary proteins.

The transition metal salts have the function of promoting denaturation of the unnecessary proteins, facilitating precipitation of the unnecessary proteins and isolation of superoxide dismutase from the unnecessary proteins with high purity and a high yield.

For weakening the bonding between superoxide dismutase and the affinity protein and other unnecessary proteins, the concentration of the monovalent inorganic neutral salt in the hemolyzed-red-blood-cell solution is in the range of 0.2 mole to its saturation, preferably in the range of 0.3 mole to 1.0 mole.

As to the transition metal salt, the appropriate concentration of the copper salt is in the range of $1 \times 10^{-4}$ mole to $2 \times 10^{-4}$ mole, while the appropriate concentration of the manganese salt is in the range of $1 \times 10^{-3}$ mole to $2 \times 10^{-3}$ mole.

During the first step, the unnecessary proteins including the affinity protein and hemoglobin are mostly caused to precipitate. The precipitated proteins are removed by filtration. At this stage, there remains a very small amount of the unnecessary proteins in the supernatant of the hemolyzed red blood cell solution.

In the second step, in order to remove the unnecessary proteins still remaining in the supernatant solution of the hemolyzed-red-blood-cell solution, the transition metal salt employed in the first step is further added to the hemolyzed-red-blood-cell solution and the hemolyzed-red-blood-cell solution is heated at temperatures ranging from 60° C. to 75° C. for 10 to 60 minutes, preferably at temperatures ranging from 60° C. to 68° C. for 15 to 30 minutes. The transition metal salt is added until the supernatant solution becomes clear while heating the hemolyzed red blood cell solution. In the particular case of the copper salt, it is added little by little in such a manner that the supernatant solution is slightly colored blue upon completion of the heating.

After cooling the hemolyzed-red-blood-cell solution, the precipitated unnecessary proteins are removed by filtration. As a result, substantially all of the unnecessary proteins are removed, while superoxide dismutase remains in the filtrate without being denaturated.

The filtrate is dialyzed against deionized water and/or a conventional buffer solution to remove the monovalent neutral salt and the transition metal salt therefrom.

From the thus obtained solution, superoxide dismutase is obtained in its pure state by a high purification process including separation by use of dialysis, DEAE cellulose column chromatography and gel-filtration.

Another process for isolating superoxide dismutase from hemolyzed red blood cells according to the present invention comprises the above-described two steps and one additional intermediate step.

In the additional intermediate step, upon completion of the first step, the transition metal salt is further added to the supernatant solution obtained in the first step in an amount ranging from $1 \times 10^{-4}$ mole to $1 \times 10^{-3}$ mole, and the supernatant solution is heated again at temperatures ranging from 60° C. to 70° C. for about 10 minutes. The unnecessary proteins precipitated in this intermediate step can be removed upon completion of this step or later. The other steps in this process are exactly the same as those in the first mentioned process according to the present invention. This second process is capable of increasing the yield of superoxide dismutase in comparison with the first mentioned process.

In connection with this intermediate step, if the amount of the transition metal salt to be added in the first step is increased beyond the amount mentioned previously, with the intermediate step omitted, the final yield of superoxide dismutase is decreased.

Specific examples of the process for isolating superoxide dismutase from red blood cells according to the present invention will now be described. In the following examples, sodium citrate was employed as an anticoagulant for the blood. Furthermore, measurement of the activity of superoxide dismutase was performed in accordance with McCord and Fridovich's method proposed in the Journal of Biochemistry, Vol. 244, 6049 (1969).

EXAMPLE 1

To 255 g of red blood cells obtained from 600 ml of fresh bovine blood, 25 g of sodium chloride, 25 mg of cupric chloride and 600 ml of water were added and mixed. The mixture was heated at 68° C. for 30 minutes. After cooling the mixture, the precipitate was removed by filtration.

25 mg of cupric chloride was added to the filtrate and the mixture was heated at 60° C. for 10 minutes.

While elevating the temperature of the mixture to 65° C. and maintaining that temperature, cupric chloride was further added little by little to the mixture until the supernatant of the mixture was colored to its maximum blue without becoming turbid. As a result, 380 mg of cupric chloride was added in total to the mixturre, taking 20 minutes, and during that period of time, the mixture was continuously heated at 65° C.

After the mixture was cooled, the precipitate was filtered off and the filtrate was dialyzed against deionized water for 48 hours and was then filtered.

The filtrate was dialyzed overnight against 0.0025 M potassium phosphate buffer (pH 7.4) and equilibrated with the same buffer. This solution was filtered, so that 850 ml of the filtrate containing 109,080 units of superoxide dismutase was obtained.

The superoxide dismutase solution was then applied on a DE 52 column (1.9×11.5 cm) (manufactured by Whatman Ltd. under the trade name of DEAE cellulose) previously equilibrated with the above-mentioned same potassium phosphate buffer, so that the superoxide dismutase solution was adsorbed to the column. Gradient elution was carried out using 400 ml of the same buffer in total, with the potassium phosphate concentration thereof ranging from 0.0025 M to 0.075 M. The active fractions of superoxide dismutase were collected and combined and dialyzed and were then lyophilized. The yield of superoxide dismutase in its lyophilized state was 43.0 mg with 96,850 units.

EXAMPLE 2

To 417 g of bovine red blood cells which had been preserved for 2 years at a temperature of −20° C., 55 g of sodium bromide, 30 mg of cupric chloride and 650 ml of water were added and mixed. The mixture was heated at 68° C. for 25 minutes. After cooling the mixture, the precipitate was removed by filtration.

20 mg of cupric chloride was added to the filtrate and the mixture was heated at 60° C. for 15 minutes.

The temperature of the mixture was elevated to 65° C. and 600 mg of cupric chloride was further added, while maintaining that temperature for 15 minutes.

After the mixture was cooled, the precipitate was filtered off, so that 1080 ml of the filtrate was obtained. The filtrate was dialyzed against deionized water for 48 hours and was then filtered.

The filtrate was dialyzed overnight against 0.0025 M potassium phosphate buffer (pH 7.4) and equilibrated with the the buffer. This solution was filtered and was then lyophilized, whereby 285 mg of superoxide dismutase with 206,400 units was obtained. The thus obtained superoxide dismutase was dissolved in 10 ml of 0.0025 M potassium phosphate buffer (pH 7.4) and the superoxide dismutase solution was then applied on a DE 52 column (1.9×11.5 cm) (manufactured by Whatman Ltd. under the trade name of DEAE cellulose) previously equilibrated with the above-mentioned same potassium phosphate buffer, so that the superoxide dismutase solution was adsorbed to the column. Gradient elution was carried out using 500 ml of the same buffer in total, with the potassium concentration thereof ranging from 0.0025 M to 0.075 M. The active fractions of superoxide dismutase were collected and combined and dialyzed and were then lyophilized. The yield of superoxide dismutase in its lyophilized state was 72.5 mg with 179,100 units.

EXAMPLE 3

To 73.5 g of lyophilized bovine red blood cells (corresponding to 210 ml of fresh bovine red blood cells), 30 g of sodium bromide, 20 mg of cupric chloride and 600 ml of water were added and mixed. The mixture was heated at 65° C. for 30 minutes. After cooling the mixture, the precipitate was removed by filtration.

320 mg of cupric chloride was added to the filtrate and the mixture was heated at 60° C. for 15 minutes.

After the mixture was cooled, the precipitate was filtered off. The filtrate was dialyzed against deionized water for 48 hours and was then filtered.

The filtrate was dialyzed overnight against 0.0025 M potassium phosphate buffer (pH 7.4) and equilibrated with the the buffer. This solution was filtered and was then applied on a DE 52 column (1.9×11.5 cm) (manufactured by Whatman Ltd. under the trade name of DEAE cellulose) previously equilibrated with the above-mentioned same potassium phosphate buffer, so that the superoxide dismutase solution was adsorbed to the column. Gradient elution was carried out using 500 ml of the same buffer in total, with the potassium phosphate concentration thereof ranging from 0.0025 M to 0.0075 M. The active fractions of superoxide dismutase were collected and combined and dialyzed and were then lyophilized. The yield of superoxide dismutase in its lyophilized state was 34.5 mg with 76,000 units.

EXAMPLE 4

To 315 g of red blood cells obtained from 30-day-old preserved human blood (in which acid-citrate-dextrose (ACD) was employed as an anticoagulant) were added 30 g of potassium chloride, 25 mg of cupric chloride and 550 ml of water and mixed. The mixture was heated at 68° C. for 30 minutes. After cooling the mixture, the precipitate was removed by filtration.

300 mg of cupric chloride was added to the filtrate and the mixture was heated at 68° C. for 20 minutes.

After the mixture was cooled, the precipitate was filtered off, whereby 920 ml of a clear, light blue filtrate was obtained and the filtrate was dialyzed against deionized water for 48 hours and was then filtered.

The activity of superoxide dismutase contained in the filtrate measured 63,600 units.

EXAMPLE 5

To 105 g of sheep red blood cells which had been preserved at a temperature of 4° C. for 15 days were added 10 g of sodium chloride, 6 mg of cupric chloride, $CuCl_2.2H_2O$, and 250 ml of water and mixed. The mixture was heated at 65° C. for 30 minutes. After cooling the mixture, the precipitate was removed by filtration.

150 mg of cupric chloride, $CuCl_2.2H_2O$, was added to the filtrate and the mixture was heated at 65° C. for 20 minutes.

After the mixture was cooled, the precipitate was filtered off. The filtrate was dialyzed against deionized water and was then filtered.

The activity of superoxide dismutase contained in the filtrate measured 19,860 units.

EXAMPLE 6

To 73.5 g of lyophilized bovine red blood cells were added 30 g of sodium nitrate, 20 mg of cupric nitrate, $Cu(NO_3)_2.3H_2O$ and 600 ml of water and mixed. The mixture was heated at 65° C. for 25 minutes. After cooling the mixture, the precipitate was removed by filtration.

280 mg of cupric nitrate, $Cu(NO_3)_2.3H_2O$, was added to the filtrate and the mixture was heated at 65° C. for 20 minutes.

After the mixture was cooled, the precipitate was filtered off. The filtrate was dialyzed against deionized water and was then filtered.

The activity of superoxide dismutase contained in the filtrate measured 94,300 units.

EXAMPLE 7

To 73.5 g of lyophilized bovine red blood cells were added 35 g of potassium nitrate, 20 mg of cupric nitrate, $Cu(NO_3)_2.3H_2O$ and 600 ml of water and mixed. The mixture was heated at 65° C. for 30 minutes. After cooling the mixture, the precipitate was removed by filtration.

300 mg of cupric nitrate, $Cu(NO_3)_2.3H_2O$, was added to the filtrate and the mixture was heated at 65° C. for 20 minutes.

After the mixture was cooled, the precipitate was filtered off. The filtrate wad dialyzed against deionized water and was then filtered.

The activity of superoxide dismutase contained in the filtrate measured 83,600 units.

EXAMPLE 8

To 210 g of frozen bovine red blood cells were added 35 g of potassium bromide, 30 mg of copper(II) bromide, $CuBr_2$, and 520 ml of water and mixed. The mixture was heated at 65° C. for 30 minutes. After cooling the mixture, precipitate was removed by filtration.

400 mg of copper(II) bromide, $CuBr_2$, was added to the filtrate and the mixture was heated at 65° C. for 20 minutes.

After the mixture was cooled, the precipitate was filtered off. The filtrate was dialyzed against deionized water and was then filtered.

The activity of superoxide dismutase contained in the filtrate measured 87,500 units.

EXAMPLE 9

To 250 g of fresh bovine red blood cells were added 15 g of lithium chloride, 20 mg of copper(I) chloride, CuCl, and 260 ml of water and mixed. The mixture was heated at 67° C. for 30 minutes. After cooling the mixture, the precipitate was removed by filtration.

320 mg of copper(I) chloride was added to the filtrate and the mixture was heated at 67° C. for 20 minutes.

After the mixture was cooled, the precipitate was filtered off. The filtrate was dialyzed against deionized water and was then filtered.

The activity of superoxide dismutase contained in the filtrate measured 104,200 units.

The following are examples of the second process including the previously mentioned intermediate step according to the present invention.

EXAMPLE 10

To 52.5 g of lyophilized bovine red blood cells were added 15 g of lithium nitrate, 20 mg of cupric nitrate, $Cu(NO_3)_2.3H_2O$ and 500 ml of water and mixed. The mixture was heated at 65° C. for 30 minutes. After cooling the mixture, the precipitate was removed by filtration.

Upon completion of that first step, 20 mg of cupric nitrate, $Cu(NO_3)_2.3H_2O$, was further added to the filtrate and the mixture was heated at 68° C. for 15 minutes. After cooling the mixture, the precipitate was removed by filtration.

1.25 g of cobalt(II) chloride, $CoCl_2.2H_2O$, was added to the filtrate and the mixture was heated at 70° C. for 30 minutes.

After the mixture was cooled, the precipitate was filtered off. The filtrate was dialyzed against deionized water and was then filtered.

The activity of superoxide dismutase contained in the filtrate measured 69,800 units.

EXAMPLE 11

To 60 g of lyophilized bovine red blood cells were added 12 g of lithium chloride, 150 mg of manganese(II) chloride, $MnCl_2.4H_2O$ and 600 ml of water and mixed. The mixture was heated at 70° C. for 30 minutes. After cooling the mixture, the precipitate was removed by filtration.

Upon completion of that first step, 15 mg of copper-(II) chloride, $CuCl_2.2H_2O$, was further added to the filtrate and the mixture was heated at 70° C. for 20 minutes. After cooling the mixture, the precipitate was removed by filtration.

2.0 g of manganese(II) chloride, $MnCl_2.4H_2O$, was added to the filtrate and the mixture was heated at 70° C. for 30 minutes.

After the mixture was cooled, the precipitate was filtered off. The filtrate was dialyzed against deionized water and was then filtered.

The activity of superoxide dismutase contained in the filtrate measured 69,750 units.

In order to confirm the effect of the monovalent inorganic neutral salt on the efficiency of separation of superoxide dismutase and on the activity of superoxide dismutase obtained, the following comparative tests were conducted by use of sodium chloride as the monovalent inorganic neutral salt.

Comparative Test 1-1

To 52.5 g of lyophilized bovine red blood cells corresponding to 150 ml of fresh bovine red blood cells) were added 15 g of sodium chloride (0.5 M), 20 mg of cupric chloride and 500 ml of water. The mixture was heated at 70° C. for 60 minutes and the formed precipitate was removed by filtration.

To the filtrate was further added 230 mg of cupric chloride and the mixture was heated at 65° C. for 20 minutes. The formed precipitate was removed by filtration.

The supernatant of the filtrate was dialyzed and was then lyophilized, so that superoxide dismutase was obtained.

The activity of the thus obtained superoxide dismutase measured 63,000 units.

Comparative Test 1-2

To 52.5 g of lyophilized bovine red blood cells (corresponding to 150 ml of fresh bovine red blood cells) were added 20 mg of cupric chloride and 500 ml of water. The mixture was heated at 70° C. for 60 minutes and the formed precipitate was removed by filtration.

To the filtrate was further added 230 mg of cupric chloride and the mixture was heated at 65° C. for 20 minutes. In the mixture, the formation of precipitate was incomplete, but the formed precipitate was removed by filtration. The filtrate was colored red brown and it appeared that complete purification by this filtration was impossible. Therefore, 220 mg of cupric chloride was further added to the filtrate, the pH of the filtrate was adjusted to be 5.6 by addition of sodium hydroxide, the mixture was heated at 65° C. for 20 minutes and the precipitate was removed by filtration. From the filtrate, a colorless supernatant (pH 5.8) was obtained.

The supernatant was dialyzed and was then lyophilized, so that superoxide dismutase was obtained.

The activity of the thus obtained superoxide dismutase measured 11,7000 units.

In Comparative Test 1-1, as the monovalent inorganic neutral salt, sodium chloride was added to the reaction mixture in the first step, while in Comparative Test 1-2, no monovalent inorganic salt was added in the first step.

The results of these two Comparative Tests were as follows:

| | Activity of Superoxide Dismutase | Ratio |
|---|---|---|
| Comparative Test 1-1 | 63,000 units | 100.0 |
| Comparative Test 1-2 | 11,700 units | 18.6 |

These results show that addition of the monovalent inorganic neutral salt significantly increased the activity of superoxide dismutase.

Furthermore, in order to confirm the effect of the second step, in which the transition metal salt is added to the reaction mixture, on the efficiency of separation of superoxide dismutase and on the activity of superoxide dismutase obtained, the following comparative tests were conducted.

Comparative Test 2-1

In this comparative test, the second step was omitted as follows:

To 52.5 g of lyophilized bovine red blood cells (corresponding to 150 ml of fresh bovine red blood cells) were added 15 g of sodium chloride, 15 mg of cupric chloride and 500 ml of water and mixed. The mixture was heated at 70° C. for 60 minutes and the formed precipitate was removed by filtration. The filtrate was colored red brown. This filtrate was dialyzed and was then lyophilized.

(1) The obtained superoxide dismutase was red brown in color.

(2) The total weight of the proteins obtained was 870 mg.

(3) The enzyme activity of superoxide dismutase was 74,400 units.

(4) The specific enzyme activity of superoxide dismutase was 86 units/protein(mg).

Comparative Test 2-2

In this comparative test, filtration of the precipitate formed in the first step was omitted.

To 52.5 g of lyophilized bovine red blood cells (corresponding to 150 ml of fresh bovine red blood cells) were added 15 g of sodium chloride, 15 mg of cupric chloride and 500 ml of water and mixed. The mixture was heated at 70° C. for 60 minutes.

After cooling the mixture, 1.9 g of cupric chloride was added to the mixture without eliminating the precipitate formed in the first step. With the pH of the mixture adjusted to be 5.6, the mixture was heated at 65° C. for 20 minutes. After cooling the mixture, the precipitate was filtered off, so that 520 ml of a colorless filtrate was obtained.

The filtrate was dialyzed and was then lyophilized.

(1) The obtained superoxide dismutase was light grey green in color.

(2) The total weight of the proteins obtained was 185 mg.

(3) The enzyme activity of superoxide dismutase was 43,200 units.

(4) The specific enzyme activity of superoxide dismutase was 238 units/protein(mg).

Comparative Test 2-3

In this comparative test, both the first step and the second step were performed.

To 52.5 g of lyophilized bovine red blood cells (corresponding to 150 ml of fresh bovine red blood cells) were added 15 g of sodium chloride, 15 mg of cupric chloride and 500 ml of water and mixed. The mixture was heated at 70° C. for 60 minutes and the formed precipitate was removed by filtration.

To the filtrate was further added 215 mg of cupric chloride at 60° C. and the mixture was heated at 65° C. for 15 minutes. After cooling the mixture, the formed precipitate was removed by filtration, so that 500 ml of the light blue filtrate was obtained.

The filtrate was dialyzed and was then lyophilized.

(1) The obtained superoxide dismutase was white.

(2) The total weight of the proteins obtained was 98 mg.

(3) The enzyme activity of superoxide dismutase was 73,250 units.

(4) The specific enzyme activity of the superoxide dismutase was 747 units/protein(mg).

The results of Comparative Tests 2-1, 2-2 and 2-3 can be summarized as follows:

| Comparative Test | Color of S.O.D. | Total Protein Weight | Enzyme Activity (Units) | Specific Enzyme Activity [Units/ Protein (mg)] |
|---|---|---|---|---|
| 2-1 | Red-Brown | 870 mg | 74,400 | 85 |
| 2-2 | Light Grey-Green | 185 mg | 43,200 | 238 |
| 2-3 | White | 98 mg | 73,250 | 747 |

S.O.D. = Superoxide Dismutase

These comparative tests indicate that omission of the second step significantly reduces the purity of the superoxide dismutase.

The embodiments described are intended to be merely exemplary and those skilled in the art will be able make variations and modifications in them without departing from the spirit and scope of the invention. For instance, in the embodiments described, precipitates formed in the course of the process for isolating superoxide dismutase from red blood cells, are removed by filtration. However, removal of such precipitates can be done by centrifugation or any other methods which are considered equivalent to those separation methods by those skilled in the art. All such modifications and variations are contemplated as falling within the scope of the claims.

What is claimed is:

1. A process for isolating superoxide dismutase from red blood cells comprising:

(a) heating hemolyzed red blood cells in the presence of at least one monovalent inorganic neutral salt and at least one transition metal salt to form a first supernatant solution and a first precipitate;

(b) removing said first precipitate;

(c) heating said first supernatant solution in the presence of at least one transition metal salt in an amount sufficient to form a clear supernatant solution and a second precipitate; and (d) removing said second precipitate.

2. The process of claim 1 further comprising heating said first supernatant solution in the presence of a transition metal in an amount between $10^{-4}$ and $10^{-3}$ mole at a temperature of from 60° C. to 70° C. to form a second supernatant solution and a second precipitate; heating said second supernatant solution in the presence of at least one transition metal salt in an amount sufficient to form said clear supernatant solution and a third precipitate; and removing said third precipitate.

3. The process of claim 2 further comprising removing said second precipitate prior to heating said second supernatant solution.

4. The process of claim 1, 2 or 3 where in the step of heating said hemolyzed red blood cells is conducted at a temperature of from 60° C. to 75° C. for 10 to 60 minutes in the presence of said monovalent inorganic neutral salt in an amount between 0.2 mole and saturation and said transition metal salt being present in an amount between $1 \times 10^{-4}$ and $2 \times 10^{-3}$ mole.

5. The process of claim 4 wherein the step of heating said hemolyzed red blood cells is conducted at a temperature between 65° C. and 70° C. for 25 to 40 minutes.

6. The process of claim 4 wherein said monovalent inorganic neutral salts are selected from the group consisting of lithium chloride, sodium chloride, potassium chloride, lithium nitrate, sodium nitrate, potassium nitrate, sodium bromide, potassium bromide, lithium bromide and ammonium bromide.

7. The process of claim 4 wherein said transition metal salts are selected from the group consisting of a water soluble salt of copper, cobalt and manganese.

8. The process of claim 7 wherein said transition metal salts are selected from the group consisting of $Cu(NO_3)_2 \cdot 3H_2O$, $CuCl_2 \cdot 2H_2O$, $CuBr_2$, $CuCl$, $MnCl_2 \cdot 4H_2O$, $CoCl_2 \cdot 2H_2O$, copper(I) chloride and copper(II) nitrate.

9. The process of claim 8 wherein said transition metal salts are copper(I) chloride or copper(II) nitrate.

10. The process of claim 4 wherein the amount of said monovalent inorganic neutral salt is between 0.3 and 1.0 mole.

11. The process of claim 1 wherein the step of heating said first supernatant solution is conducted in the presence of at least one transition metal salt in an amount equal to or greater than the amount used in the step of heating said hemolyzed red blood cells.

12. The process of claim 2 or 3 wherein the step of heating said second supernatant solution is conducted in the presence of at least one transition metal salt in an amount equal to or greater than the amount used in the step of heating said hemolyzed red blood cells.

13. The process of claim 1 wherein the step of heating said first supernatant solution is conducted at a temperature of from 60° C. to 75° C. for 10 to 60 minutes.

14. The process of claim 2 or 3 wherein the step of heating said second supernatant solution is conducted at a temperature of from 60° C. to 75° C. for 10 to 60 minutes.

15. The process of claim 13 wherein said heating step is conducted at a temperature of from 60° C. to 68° C. for 15 to 30 minutes.

16. The process of claim 14 wherein said heating step is conducted at a temperature of from 60° C. to 68° C. for 15 to 30 minutes.

17. The process of claim 1, 2 or 3 further comprising dialyzing said clear supernatant solution and isolating superoxide dismutase from said dialyzed supernatant solution.

18. The process of claim 17 wherein the step of dialyzing said clear supernatant solution is conducted in the presence of at least one deionized water or a buffer solution.

19. The process of claim 1, 2 or 3 wherein said hemolyzed red blood cells are a mixture of red blood cells and water in a ratio of 1:1–4.

* * * * *